(12) United States Patent
Yamamoto et al.

(10) Patent No.: US 11,026,961 B2
(45) Date of Patent: Jun. 8, 2021

(54) USE OF BIOSURFACTANT

(71) Applicants: HIROSHIMA UNIVERSITY, Higashihiroshima (JP); TOYOBO CO., LTD., Osaka (JP)

(72) Inventors: Shuhei Yamamoto, Osaka (JP); Masao Kitabayashi, Osaka (JP); Keiichi Hisaeda, Ozu (JP); Naoki Isobe, Higashihiroshima (JP)

(73) Assignees: HIROSHIMA UNIVERSITY, Higashihiroshima (JP); TOYOBO CO., LTD., Osaka (JP)

( * ) Notice: Subject to any disclaimer, the term of this patent is extended or adjusted under 35 U.S.C. 154(b) by 22 days.

(21) Appl. No.: 16/473,555

(22) PCT Filed: Dec. 18, 2017

(86) PCT No.: PCT/JP2017/045273
§ 371 (c)(1),
(2) Date: Jun. 25, 2019

(87) PCT Pub. No.: WO2018/123680
PCT Pub. Date: Jul. 5, 2018

(65) Prior Publication Data
US 2020/0138842 A1    May 7, 2020

(30) Foreign Application Priority Data

Dec. 27, 2016 (JP) .............................. JP2016-252947
Dec. 27, 2016 (JP) .............................. JP2016-252952

(51) Int. Cl.
*A61K 31/7032* (2006.01)
*A61K 9/00* (2006.01)
*A61P 15/14* (2006.01)

(52) U.S. Cl.
CPC ........ *A61K 31/7032* (2013.01); *A61K 9/0017* (2013.01); *A61P 15/14* (2018.01)

(58) Field of Classification Search
CPC .... A61K 31/7032; A61K 9/0017; A61P 15/14
USPC ......................................................... 514/25
See application file for complete search history.

(56) References Cited

U.S. PATENT DOCUMENTS

| 2010/0249058 A1* | 9/2010 | Ito .......................... A23K 50/75 |
| | | 514/53 |
| 2010/0272690 A1* | 10/2010 | Gandhi .................. D06M 16/00 |
| | | 424/93.5 |
| 2014/0134144 A1 | 5/2014 | Ametaj et al. |

FOREIGN PATENT DOCUMENTS

| EP | 2074889 A | 7/2009 |
| JP | H07-109227 A | 4/1995 |
| JP | 2001-224317 A | 8/2001 |
| JP | 2005-041798 A | 2/2005 |
| JP | 2012-126657 A | 7/2012 |
| JP | 2016-094398 A | 5/2016 |
| JP | 2016-522796 A | 8/2016 |
| WO | WO 2014/145828 A1 | 9/2014 |

OTHER PUBLICATIONS

Morita et al. Characterization of the genus *Pseudozyma* by the formation of glycolipid biosurfactants, mannosylerythritol lipids. FEMS Yeast Res 7 (2007) 286-292. (Year: 2007).*
Kitamoto et al., "Self-assembling properties of glycolipid biosurfactants and their potential applications," *Current Opinion in Colloid & Interface Science*, 14(5): 315-328 (2009).
Japanese Patent Office, International Search Report in International Patent Application No. PCT/JP2017/045273 (dated Jan. 30, 2018).
Mungube et al., "Reduced Milk Production in Udder Quarters with Subclinical Mastitis and Associated Economic Losses Crossbred Dairy Cows in Ethiopia," *Trop. Anim. Health Prod.*, 37(6): 503-512 (2005).
Yamamoto et al., "Production of a Novel Mannosylerythritol Lipid Containing a Hydroxy Fatty Acid from Castor Oil by *Pseudozyma tsukubaensis*," *J. Oleo Sci.*, 62(6): 381-389 (2013).
European Patent Office, Communication Pursuant to Rule 164(1) EPC in European Patent Application No. 17889253.5 (dated Jun. 24, 2020).

* cited by examiner

*Primary Examiner* — Yih-Horng Shiao
(74) *Attorney, Agent, or Firm* — Leydig, Voit & Mayer, Ltd.

(57) ABSTRACT

An object is to provide a novel means for ameliorating mastitis or improving milk production. An ameliorating or therapeutic agent for mastitis that contains a biosurfactant, or a milk production promoting agent that contains a biosurfactant, is provided.

2 Claims, 3 Drawing Sheets

* $P<0.05$

USE OF BIOSURFACTANT

CROSS-REFERENCE TO RELATED APPLICATIONS

This patent application is the U.S. national phase of International Patent Application No. PCT/JP2017/045273, filed Dec. 18, 2017, which claims the benefit of Japanese Patent Application No. 2016-252947, filed on Dec. 27, 2016, and Japanese Patent Application No. 2016-252952, filed on Dec. 27, 2016, which are incorporated by reference in their entireties herein.

TECHNICAL FIELD

Techniques for ameliorating or treating mastitis and promoting milk production are disclosed.

BACKGROUND ART

Among dairy cow diseases, mastitis is a disease that develops in the mammary gland directly related to the productivity of milk; therefore, its economic impact is very large. As a treatment for mastitis, antibiotics are generally administered. However, the antibiotics used may problematically remain in the body and the shipment of raw milk is restricted for a certain period of time, thus resulting in large economic loss. Therefore, it is desirable to avoid the use of antibiotics as far as possible.

Under such circumstances, there have been reported attempts to prevent or treat mastitis by feeding dairy cows with a component other than antibiotics (for example, a component derived from a natural product). For example, Patent Literature (PTL) 1 proposes a composition for preventing and/or treating mastitis, which comprises, as an active ingredient, a culture composition obtained from a culture of a microorganism belonging to the genus *Aureobasidium* sp. Further, Patent Literature (PTL) 2 proposes a livestock mastitis preventive and/or therapeutic composition comprising live baker's yeast as an active ingredient. These compositions are assumed to be administered to livestock, for example, by incorporation into feed.

On the other hand, mammals need milk secretion or production depending on the situation, regardless of the species. In particular, milk of ruminants is widely used as food, either as is or after being processed; therefore, improved productivity of milk is desired. Milk production has been conventionally improved mainly by interbreeding using high milk yield species, improving the growth environment, and improving feed.

On the other hand, "biosurfactant" is a generic term for substances that are produced by microorganisms and that have surfactant action and emulsifying action. Biosurfactants have been reported to have high biodegradability and various physiological effects (Patent Literature (PTL) 3).

CITATION LIST

Patent Literature

PTL 1: JP2012-126657A
PTL 2: JP2001-224317A
PTL 3: JP2016-94398A

SUMMARY OF INVENTION

Technical Problem

An object is to provide a novel means for ameliorating or treating mastitis. Another object is to provide a novel means for improving milk production.

Solution to Problem

As a result of extensive studies to solve such problems, the present inventors found that (1) biosurfactants have an ameliorating or therapeutic action on mastitis, and (2) biosurfactants have a promoting action on milk production or secretion. The inventors have conducted further research based on these findings, and provide the following representative subject matter.

Item 1
An ameliorating or therapeutic agent for mastitis comprising a biosurfactant.

Item 2
The ameliorating or therapeutic agent for mastitis according to Item 1, which is for a ruminant.

Item 3
The ameliorating or therapeutic agent for mastitis according to Item 1 or 2, wherein the ameliorating or therapeutic agent is topically applied to an udder or breast.

Item 4
The ameliorating or therapeutic agent for mastitis according to Item 3, wherein the topical application is continued at a frequency of at least once a day for at least 3 days.

Item 5
A method of ameliorating or treating mastitis, comprising topically applying a biosurfactant to an udder of a ruminant.

Item A
A milk production promoting agent comprising a biosurfactant.

Item B
The milk production promoting agent according to Item A, which is for a ruminant.

Item C
The milk production promoting agent according to Item A or B, which is topically applied to an udder or breast.

Item D
The milk production promoting agent according to Item C, wherein the topical application is continued at a frequency of at least once a day for at least 3 days.

Item E
A method for promoting milk production, comprising topically applying a biosurfactant to an udder of a ruminant.

Item F
The method for promoting milk production according to Item E, wherein the topical application is performed at a frequency of at least once a day.

Advantageous Effects of Invention

A means for ameliorating and treating mastitis can be provided. A means for promoting milk production or secretion can be provided. These enable more efficient milk production.

DESCRIPTION OF EMBODIMENTS

Figure 1:
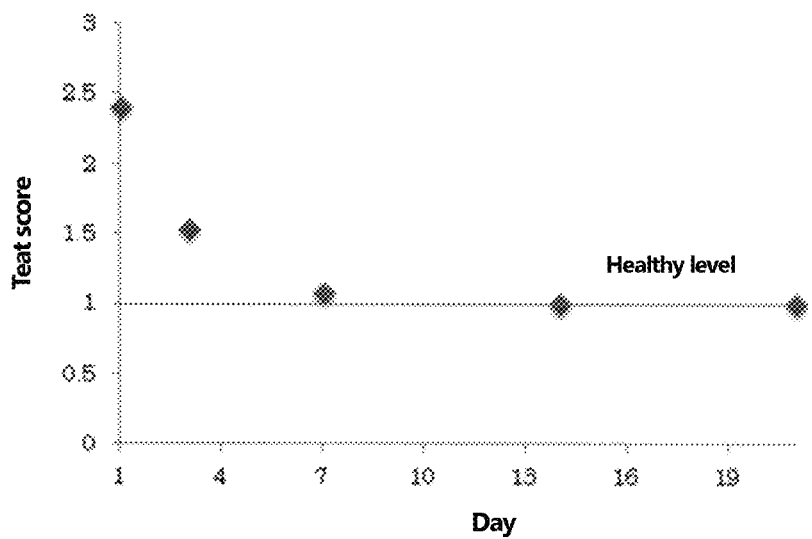
FIG. 1 shows changes in the teat score of dairy cows with mastitis by application of a biosurfactant.

The kind of biosurfactant is not particularly limited and any biosurfactant can be used. Examples of biosurfactants include mannosyl erythritol lipids (MELs), mannosyl mannitol lipids (MMLs), mannosyl sorbitol lipids (MSLs), mannosyl arabitol lipids (MAraLs), mannosyl ribitol lipids (MRLs), cellobiose lipids, rhamnolipids, trehalose lipids, sophorolipids, and surfactins. MELs, MMLs, MSLs, MAraLs, MRLs, and the like are also collectively referred to as mannosyl alditol lipids (MALs). In one embodiment, the biosurfactant preferably has the action of forming a lamellar structure and/or a vesicle. The biosurfactant is preferably, for example, an MEL.

MELs have a structure represented by the following formula (1):

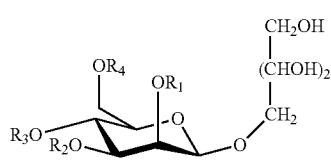

(1)

(wherein $R_1$ and $R_2$ each independently represent $C_{2-24}$ aliphatic acyl, and $R_3$ and $R_4$ each independently represent hydrogen or acetyl.)

MELs are classified into 4 types (MEL-A, MEL-B, MEL-C, and MEL-D) according to the kinds of $R_3$ and $R_4$ in formula (1). MEL-A has a structure wherein $R_3$ and $R_4$ are both acetyl. MEL-B has a structure wherein $R_3$ is hydrogen and $R_4$ is acetyl. MEL-C has a structure wherein $R_3$ is acetyl and $R_4$ is hydrogen. MEL-D has a structure wherein $R_3$ and $R_4$ are both hydrogen. In one embodiment, the MEL is preferably MEL-B.

In one embodiment, regardless of the type of MEL, $R_1$ and $R_2$ in formula (1) are preferably aliphatic acyl having 4 to 24 carbon atoms, and more preferably 8 to 14 carbon atoms.

MEL can exist as its two optical isomers (4-O-β-D-mannopyranosyl-meso-erythritol (abbreviated as "4-O-β-MEL") and 1-O-β-D-mannopyranosyl-meso-erythritol (abbreviated as "1-O-β-MEL") in the structure of the erythritol moiety. In one embodiment, the MEL is preferably 1-O-β-MEL. In another embodiment, the MEL is preferably 4-O-β-MEL. In a preferred embodiment, the MEL preferably has a structure represented by the following formula (2):

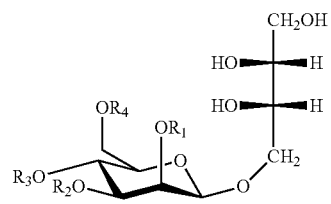

(2)

In the MEL of formula (2), $R_1$ and $R_2$ are preferably $C_{4-24}$ aliphatic acyl, and more preferably $C_{8-14}$ aliphatic acyl. In one embodiment, $R_3$ in the MEL of formula (1) is preferably hydrogen. In one embodiment, $R_4$ in the MEL of formula (1) is preferably acetyl.

Biosurfactants are commercially available and can also be obtained by chemical synthesis or microorganism culturing. In one embodiment, producing a biosurfactant by culturing a microorganism is preferable.

Examples of microorganisms that produce MEL include microorganisms belonging to the genera *Pseudozyma, Moesziomyces, Ustilago, Sporisorium nigra, Melanopsi-chium,* and *Kurtzmanomyces*. Examples of preferred microorganisms belonging to the genus *pseudozyma* include *Pseudozyma antarctica, Pseudozyma parantarctica, Pseudozyma rugulosa, Pseudozyma siamensis, Pseudozyma shanxiensis, Pseudozyma crassa, Pseudozyma churashimaensis, Pseudozyma aphidis, Pseudozyma hubeiensis, Pseudozyma tsukubaensis,* and the like. Examples of preferred microorganisms belonging to the genus *Moesziomyces* include *Moesziomyces antarcticus, Moesziomyces aphidis,* and the like. Examples of preferred microorganisms belonging to the genus *Ustilago* include *Ustilago hordei, Ustilago maydis,* and the like. Examples of preferred microorganisms belonging to the genus *Sporisorium* include *Sporisorium reilianum, Sporisorium scitamineum,* and the like. Examples of preferred microorganisms belonging to the genus *Melanopsichium* include *Melanopsichium pennsylvanicum* and the like. Examples of preferred microorganisms belonging to the genus *Kurtzmanomyces* include *Kurtzmanomyces* sp. I-11 and the like. In a preferred embodiment, MEL-producing microorganisms are microorganisms belonging to the genus *pseudozyma,* and more preferably microorganisms belonging to *Pseudozyma tsukubaensis.* More specifically, *Pseudozyma tsukubaensis* 1E5 (JCM 16987 strain), NBRC1940 (ATCC24555, CBS422.96, CBS6389, DBVPG6988, PYCC4855, JCM10324, MUCL29894, NCYC1510, and NRRLY-7792) are preferable. These microorganisms can be used singly, or in a combination of two or more. Microorganisms belonging to *Pseudozyma tsukubaensis* selectively produce 1-O-β-MEL-B.

The production of MEL using a microorganism can be performed under any conditions by any method. For example, MEL can be produced by culturing a microorganism. The medium to be used is not particularly limited. For example, using a carbohydrate, such as glucose, sucrose, or blackstrap molasses is preferable. In addition to, or in place of, a carbohydrate, a fat and/or an oil can also be used as a carbon source. The kind of fat and/or oil is not particularly limited. For example, vegetable fats and oils, fatty acids, or esters thereof can be added.

In one embodiment, adding vegetable fat and/or oil to the culture medium is preferred. The kind of vegetable oil is not particularly limited, and can be appropriately selected according to, for example, the type of MEL desired. Examples of vegetable fats and oils include soybean oil, olive oil, rapeseed oil, safflower oil, sesame oil, palm oil, sunflower oil, coconut oil, cocoa butter, castor oil, and the like. Examples of fatty acids include caprylic acid, capric acid, lauric acid, myristic acid, palmitic acid, stearic acid, oleic acid, linoleic acid, linolenic acid, arachidonic acid, behenic acid, nervonic acid, and the like. These fatty acids can be used singly, or in a combination of two or more. In one embodiment, the fatty acid is preferably oleic acid.

In one embodiment, a microorganism that produces MEL can be cultured in a medium containing only glucose as a carbon source. As a nitrogen source, a combination of an organic nitrogen source and an inorganic nitrogen source can be used. For example, as the organic nitrogen source, two or more members selected from the group consisting of yeast extracts, malt extracts, peptone, polypeptone, corn steep liquor, casamino acid, and urea can be used in combination, or one of them can be used alone. As the inorganic nitrogen source, one member or a combination of two or more members selected from the group consisting of sodium nitrate, potassium nitrate, ammonium nitrate, ammonium sulfate, and ammonia can be used. In another embodiment, a method of producing mannosyl erythritol lipid is provided, which comprises culturing a microorganism capable of producing mannosyl erythritol lipid in a medium containing fatty acid and glycerin.

The amount of fatty acid and the amount of fat and/or oil are not particularly limited. For example, fatty acid and fat and/or oil can be added in such an amount as to each achieve a concentration of 0.1 to 30 volume % in the medium.

The conditions for culturing the microorganism are not particularly limited. For example, culture can be performed at pH 4 to 8, preferably pH 5 to 6, and at a temperature of 20 to 35° C., preferably 22 to 28° C., for 3 to 7 days. MEL can be recovered from the culture solution according to a usual method.

The ameliorating or therapeutic agent for mastitis, or the milk production promoting agent may contain any other component as long as it does not impair the mastitis ameliorating or therapeutic action, or the milk production promoting action. Examples of such other ingredients include the following: water; alcohols, such as ethanol; color pigments, such as tar pigments and iron oxide; preservatives, such as paraben and phenoxyethanol; squalanes, such as olive squalane, rice squalane, and shark squalane; silicone oils, such as dimethylpolysiloxane and cyclic silicone; hydrocarbons, such as paraffin, liquid paraffin, vaseline, olefin oligomers, and squalane; vegetable oils, such as jojoba oil, olive oil, macadamia nut oil, castor oil, safflower oil, sunflower oil, avocado oil, canola oil, apricot kernel oil, rice germ oil, and rice bran oil; triglycerides, such as glyceryl triacetyl hydroxystearate, glyceryl triacetyl ricinoleate, triisopalmitic acid glyceride, glyceryl triisostearate, glyceryl triundecanoate, glyceryl trihydroxystearate, glyceryl trioleate, glyceryl tri(caprylate/caprate), glyceryl tri (caprylate/caprate/myristate/stearate), glyceryl tri(caprylate/caprate/laurate), glyceryl tri(caprylate/caprate/linoleate), glyceryl tricaprate, glyceryl tritallowate, trimyristic acid glyceride, glyceryl tristearate, glyceryl tripalmitate, glyceryl tri-2-heptylundecanoate, glyceryl tribehenate, glyceryl trimyristate, glyceryl tricocoate, glyceryl trilaurate, glyceryl trilanolate, glyceryl 2-ethylhexanoate, glyceryl trilinoleate, and like synthetic glycerides; waxes, such as beeswax, Japan wax (*Rhus succedanea* fruit wax), and carnauba wax; ester oils, such as octyldodecyl myristate, cetyl palmitate, isostearyl isostearate and isopropyl myristate; higher alcohols, such as cetanol, behenyl alcohol, isostearyl alcohol, jojoba alcohol, oleyl alcohol, stearyl alcohol, and long chain branched aliphatic alcohol; cholesterol, phytosterol, branched fatty acid cholesterol ester, macadamia nut fatty acid phytosteryl ester, and like sterols, and derivatives thereof; processed oils, such as hardened oil; higher fatty acids, such as stearic acid, myristic acid, long chain iso-fatty acid, and long chain anteiso-fatty acid; ethers, such as dicapryl ether; and terpenes, such as limonene and hydrogenated bisabolol; anionic surfactants, such as sodium cetyl sulfate, and N-stearoyl-L-glutamate; nonionic surfactants, such as polyhydric alcohol fatty acid ester (excluding polyoxyethylene hydrogenated castor oil), modified silicone, and sucrose ester; cationic surfactants, such as tetraalkyl ammonium salts; amphoteric surfactants, such as betaine, sulfobetaine, and sulfoamino acid surfactants; natural surfactants, such as lecithin, lysophosphatidylcholine, ceramide, and cerebroside; pigments, such as titanium oxide and zinc oxide; antioxidants, such as dibutylhydroxytoluene; inorganic salts, such as sodium chloride, magnesium chloride, sodium sulfate, and potassium nitrate; organic acid salts, such as sodium citrate, potassium acetate, sodium succinate, sodium aspartate, sodium lactate, gamma-aminobutyric acid, and lipoic acid; salts, such as ethanolamine hydrochloride, ammonium nitrate, and arginine hydrochloride; chelators, such as edetic acid; neutralizers, such as potassium hydroxide, diisopropanolamine, and triethanolamine; biopolymers, such as hyaluronic acid and collagen; placenta extracts; UV absorbers, such as hydroxymethoxybenzophenone sulfonate; vitamin A and derivatives thereof, such as retinol, retinol acetate, and retinol palmitate; vitamin E and derivatives thereof, such as α-tocopherol, γ-tocopherol, δ-tocopherol, tocopherol nicotinate, and tocopherol acetate; oil-soluble vitamin C derivatives, such as ascorbyl palmitate, ascorbyl stearate, and ascorbyl tetraisostearate; xanthan gum, β-glucan, polysaccharides extracted from oat, white jelly fungus, etc., carrageenan, alginic acid, agar, and like seaweed extracts, carboxyvinyl polymers, pectin, alkyl-modified carboxyvinyl polymers, and like water-soluble polymers; and polyhydric alcohols, such as dipropylene glycol, 1,3-butylene glycol, glycerol, propylene glycol, sorbitol, maltitol, diglycerol, raffinose, and hexylene glycol.

The ameliorating or therapeutic agent for mastitis, or the milk production promoting agent can be in any form as long as it can ameliorate or treat mastitis, or it can promote milk production. The ameliorating or therapeutic agent for mastitis, or the milk production promoting agent may consist only of a biosurfactant, or can be combined with any excipient that does not impair the mastitis ameliorating or therapeutic action, or the milk production promoting action, and formulated into any form suitable for parenteral administration, oral administration, or external administration (e.g., drugs, quasi-drugs, foods, cosmetics, veterinary drugs, animal foods, and animal cosmetics). In one embodiment, the ameliorating or therapeutic agent for mastitis, or the milk production promoting agent is preferably in a form suitable for topical administration (e.g., external preparation). The ameliorating or therapeutic agent for mastitis, or the milk production promoting agent may be, for example, in a form selected from the group consisting of lotions, emulsions, gels, creams, ointments, sprays, powders, and the like. In one embodiment, the ameliorating or therapeutic agent for mastitis, or the milk production promoting agent may be in a form suitable for non-topical administration. Examples of forms include liquids, tablets, capsules, powders, granules, and the like. In another embodiment, the ameliorating or therapeutic agent for mastitis, or the milk production promoting agent, may be in the form of an injectable preparation.

The amount of biosurfactant contained in the ameliorating or therapeutic agent for mastitis or the milk production-promoting agent is not particularly limited, as long the mastitis ameliorating or therapeutic action can be provided, and any amount can be selected. For example, the ameliorating or therapeutic agent for mastitis, or the milk production promoting agent can contain a biosurfactant in an amount of 0.1 to 30 mass %, preferably 0.5 to 20% mass %.

The subject to which the ameliorating or therapeutic agent for mastitis or the milk production promoting agent is applied is not particularly limited as long as the mastitis ameliorating or therapeutic action or the milk production promoting action can be provided. The subject may be, for example, a mammal. Preferably, the subject is a female mammal capable of producing milk. In one embodiment, the subject is a non-human mammal, preferably a ruminant. Examples of ruminants include cattle, goats, sheep, deer, camels, bison, and the like. From the viewpoint of widespread livestock use, the subject is preferably selected from the group consisting of cattle, goats, sheep, horses, and pigs, and more preferably cattle, and particularly preferably dairy cows. In another embodiment, the subject may be pets, such as dogs and cats.

In one embodiment, the ameliorating or therapeutic agent for mastitis or the milk production promoting agent is preferably used by direct application to the udder or breast and/or teat or nipple of a subject. The conditions, such as the amount of application, application period, and application frequency, are not particularly limited, and can be appropriately set according to the kind of subject (e.g., livestock), age, body weight, time, and the like. For example, for dairy cows, it is preferable to set the conditions for application according to the period (e.g., perinatal period, lactation period, etc.), stress conditions, nutritional state, age, etc.

The ameliorating or therapeutic agent for mastitis, or the milk production promoting agent is preferably applied continuously for several days to several weeks. For example, the ameliorating or therapeutic agent for mastitis, or the milk production promoting agent can be continuously applied in an amount of 0.01 to 5 g, preferably 0.1 to 1 g, per breast per day for 3 days or more, preferably 5 days or more, more preferably 8 days or more, and still more preferably 10 days or more.

In one embodiment, the timing for applying the ameliorating or therapeutic agent for mastitis or the milk production promoting agent can be set, for example, to be before or after the wipe-cleaning operation or milking.

EXAMPLES

The present invention is described below in more detail with reference to Examples. However, the scope of the invention is not limited to these Examples.

Production Example 1

*Pseudozyma tsukubaensis* (NBRC 1940) was cultured in YM medium with shaking at 26° C. for 48 hours using a 500-mL volume Sakaguchi flask. Using the obtained solution as a seed culture solution, culturing was performed with aeration and agitation in YM medium (containing 5% olive oil) at a culturing temperature of 26° C. for 7 days using a 10-L volume jar fermenter. An equal volume of ethyl acetate was added to the culture solution and stirred and the resulting liquid was separated into phases. An appropriate amount of anhydrous sodium sulfate was added to the ethyl acetate layer, and the mixture was allowed to stand for 30 minutes, and then concentrated at reduced pressure under heating conditions to obtain crude MEL-B. This crude MEL-B was subjected to silica gel column chromatography. Elution was performed using, as eluents, chloroform:acetone=1:0, chloroform:acetone=9:1, chloroform:acetone 1:1, and chloroform:acetone=3:7, and chloroform:acetone=0:1. The MEL-B fraction was collected and concentrated to obtain purified MEL-B. This purified MEL-B was added to a 1,3 v-butylene glycol solution (50 v/v %) to a final concentration of 10 w/v % and dissolved to obtain a test solution.

Test Example 1

Figure 2:
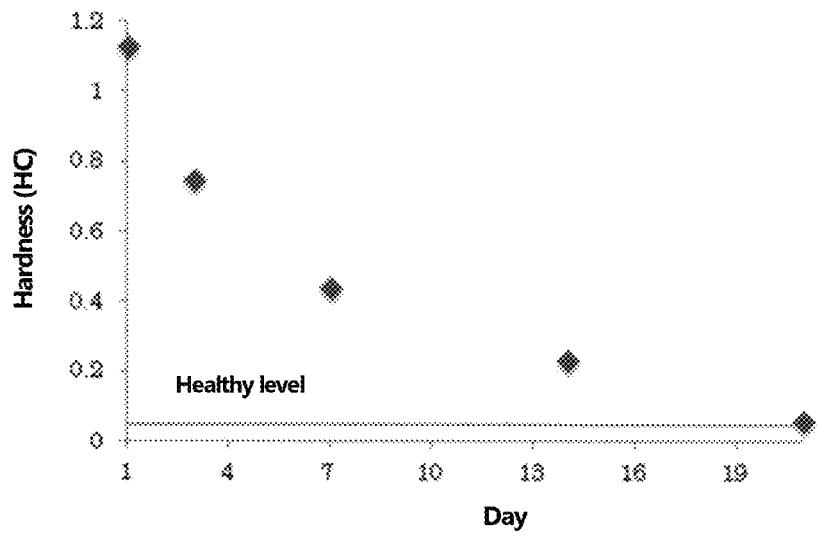
FIG. 2 shows changes in the hardness of teats of dairy cows with mastitis by application of a biosurfactant.
Figure 3:
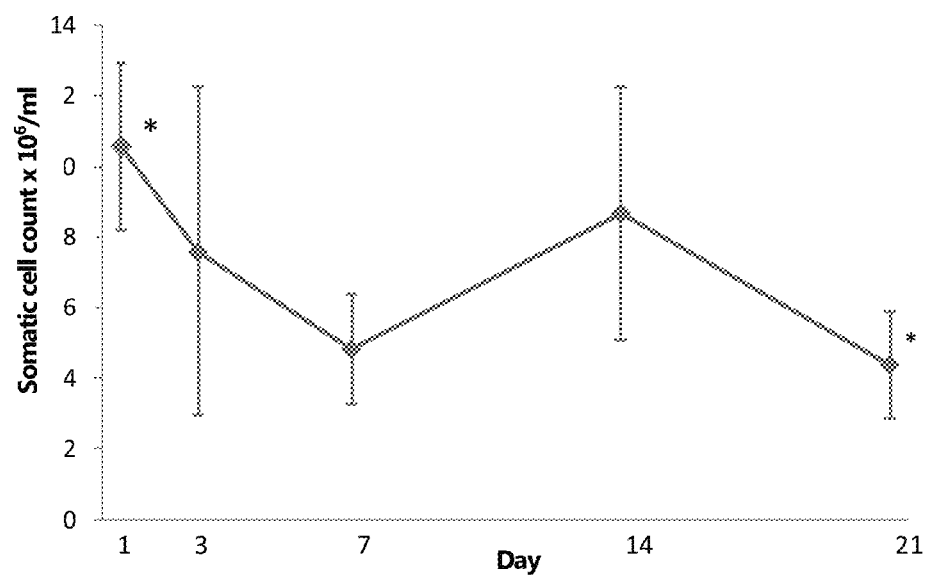
FIG. 3 shows changes in the somatic cell count in milk from affected udder by application of a biosurfactant.

After milking in the afternoon, the test solution was uniformly applied to the udders and teats of seven dairy cows with mastitis in an amount of 5 to 6 mL per udder. Milking was performed twice a day (morning and afternoon). This operation was continued for seven days. During this period and thereafter, the teat score (Mein et al.) and induration of the udders were measured using a muscle hardness tester (PPLS Digital Hardness Tester, Type C, Pepaless Co., Ltd., Model No. TR-DHNC). As a result, as shown in FIG. 1, the average teat score was improved from 2.4 to 1.0 (healthy state) by the MEL application. Further, as shown in FIG. 2, the degree of induration of the udders measured with the muscle hardness tester also decreased from 1.13 to 0.06 (the hardness of healthy dairy cow's breasts). Further, the number of somatic cells was measured by a fluoro-optical somatic cell counting method. As shown in FIG. 3, a significant decrease in the somatic cell count by the MEL application was observed after 21 days. The results thus confirmed that biosurfactants, such as MEL, significantly ameliorate mastitis.

Test Example 2

Figure 4:
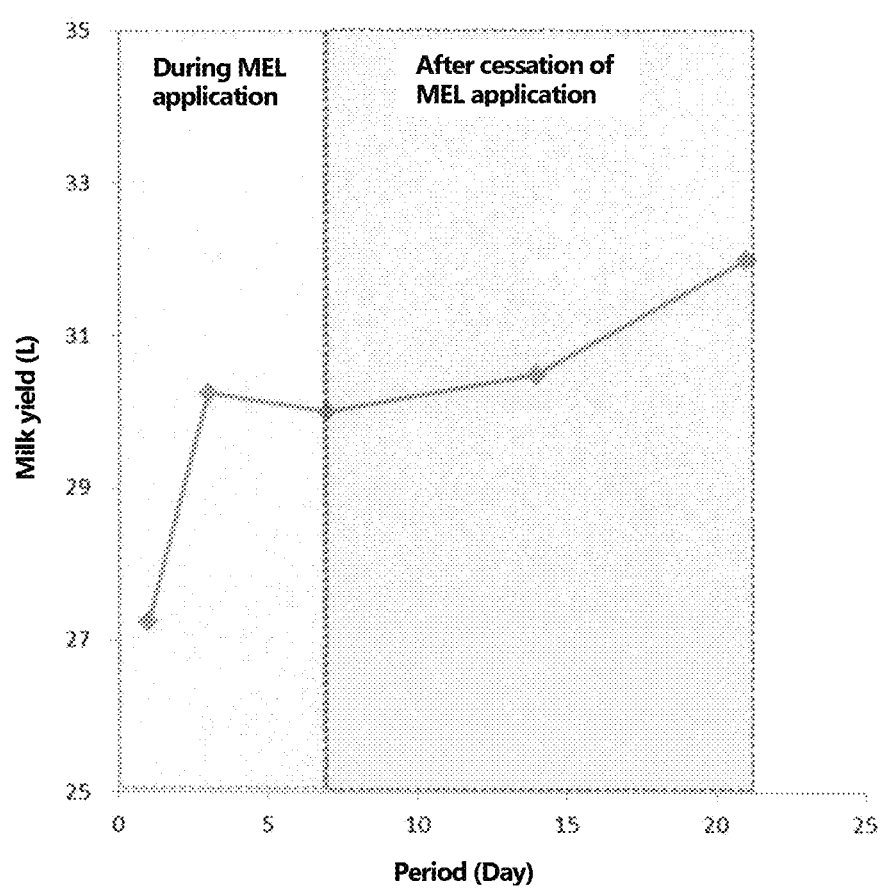
FIG. 4 shows changes in the milk yield of dairy cows by application of a biosurfactant.

After milking in the afternoon, the test solution was uniformly applied to the udders and teats of four dairy cows in an amount of 5 to 6 mL per udder. Milking was performed twice a day (morning and afternoon). This operation was continued for seven days, and the daily milk yield per head was measured. FIG. 4 shows changes in the average milk yield measured. As shown in FIG. 4, the results confirmed that the MEL application increases the milk yield of dairy cows, and that the milk yield-increasing effect by MEL is maintained, even after cessation of the MEL application.

The invention claimed is:

1. A method for ameliorating or treating mastitis, comprising topically applying an effective amount of a biosurfactant to an udder of a ruminant in need thereof at a frequency of at least once a day for at least 7 days.

2. A method for promoting milk production, comprising topically applying an effective amount of a biosurfactant to an udder of a ruminant in need thereof at a frequency of at least once a day for at least 3 days.

* * * * *